(12) United States Patent
Arramon

(10) Patent No.: US 12,263,098 B2
(45) Date of Patent: Apr. 1, 2025

(54) INTERVERTEBRAL PROSTHETIC DISC PLACEMENT AND REMOVAL SYSTEMS

(71) Applicant: Simplify Medical Pty Ltd, Melbourne (AU)

(72) Inventor: Yves Arramon, Sunnyvale, CA (US)

(73) Assignee: Globus Medical Inc., Audubon, PA (US)

( * ) Notice: Subject to any disclaimer, the term of this patent is extended or adjusted under 35 U.S.C. 154(b) by 506 days.

(21) Appl. No.: 17/457,076

(22) Filed: Dec. 1, 2021

(65) Prior Publication Data

US 2022/0087832 A1   Mar. 24, 2022

Related U.S. Application Data

(63) Continuation of application No. 16/861,079, filed on Apr. 28, 2020, now Pat. No. 11,219,536.

(60) Provisional application No. 62/841,359, filed on May 1, 2019.

(51) Int. Cl.
  *A61F 2/46* (2006.01)
  *A61F 2/44* (2006.01)

(52) U.S. Cl.
  CPC ............ *A61F 2/4611* (2013.01); *A61F 2/442* (2013.01); *A61F 2002/4619* (2013.01)

(58) Field of Classification Search
  CPC .......... A61F 2/4611; A61F 2/442–4425; A61F 2/4684; A61F 2002/443
  See application file for complete search history.

(56) References Cited

U.S. PATENT DOCUMENTS

| | | | |
|---|---|---|---|
| 4,997,432 A * | 3/1991 | Keller | A61B 17/2804 600/219 |
| 7,294,134 B2 | 11/2007 | Weber | |
| 7,442,211 B2 | 10/2008 | De Villiers et al. | |
| 7,531,001 B2 | 5/2009 | De Villiers et al. | |
| 7,575,599 B2 | 8/2009 | De Villiers et al. | |

(Continued)

FOREIGN PATENT DOCUMENTS

| | | |
|---|---|---|
| JP | 2009279413 A | 12/2009 |
| KR | 20060114712 A | 11/2006 |

(Continued)

OTHER PUBLICATIONS

International Search Report and Written Opinion for PCT/AU2020/000037 on Jul. 31, 2020.

*Primary Examiner* — Eduardo C Robert
*Assistant Examiner* — Michelle C Green

(57) ABSTRACT

Embodiments of the disclosure provide systems and methods of removing a core from an intervertebral prosthetic disc. The method may include: securing a multipart prosthetic disc to a distal end of a removal instrument by grasping at least a portion of the multipart prosthetic disc between a pair of core removal arms on the placement instrument; inserting the pair of core removal arms between two prosthetic disc plates of the intervertebral prosthetic disc to distract the plates away from one another; and removing the core from the intervertebral prosthetic disc with the removal instrument. The removal instrument may include: an inner shaft connected to the pair of core removal arms; and an outer shaft movable with respect to the inner shaft and including an activation mechanism for causing the arms to grasp the core for removal.

10 Claims, 9 Drawing Sheets

(56) References Cited

U.S. PATENT DOCUMENTS

| | | | |
|---|---|---|---|
| 7,585,326 B2 | 9/2009 | De Villiers et al. | |
| 7,637,913 B2 | 12/2009 | De Villiers et al. | |
| 7,753,956 B2 | 7/2010 | De Villiers et al. | |
| 8,206,449 B2 | 6/2012 | Jansen et al. | |
| 8,343,163 B1 | 1/2013 | Arambula et al. | |
| 8,685,035 B2 | 4/2014 | De Villiers et al. | |
| 8,764,833 B2 | 7/2014 | De Villiers et al. | |
| 8,808,384 B2 | 8/2014 | Arramon | |
| 9,011,544 B2 | 4/2015 | Arramon et al. | |
| 9,351,846 B2 | 5/2016 | De Villiers et al. | |
| 10,206,785 B2 | 2/2019 | Arramon et al. | |
| 10,426,628 B2 | 10/2019 | Arramon et al. | |
| 2003/0229355 A1* | 12/2003 | Keller | A61F 2/4611 606/247 |
| 2005/0015095 A1 | 1/2005 | Keller | A61F 2/4611 606/99 |
| 2005/0027300 A1* | 2/2005 | Hawkins | A61F 2/4684 606/86 R |
| 2005/0033305 A1 | 2/2005 | Schultz | A61F 2/4611 606/99 |
| 2006/0064107 A1* | 3/2006 | Bertagnoli | A61F 2/4611 606/99 |
| 2006/0085011 A1 | 4/2006 | Filippi et al. | |
| 2006/0149284 A1 | 7/2006 | McCormack et al. | |
| 2008/0294260 A1 | 11/2008 | Gray | |
| 2009/0254182 A1 | 10/2009 | Kovarik | A61L 27/12 623/17.11 |
| 2010/0331988 A1 | 12/2010 | Marnay et al. | |
| 2011/0264152 A1 | 10/2011 | Weiman | A61B 17/1757 606/86 R |
| 2011/0301612 A1* | 12/2011 | Richter | A61F 2/4425 606/99 |
| 2019/0000647 A1 | 1/2019 | De Villiers et al. | |

FOREIGN PATENT DOCUMENTS

| | | |
|---|---|---|
| WO | 2008034140 A2 | 3/2008 |
| WO | 2010056355 A3 | 5/2010 |

\* cited by examiner

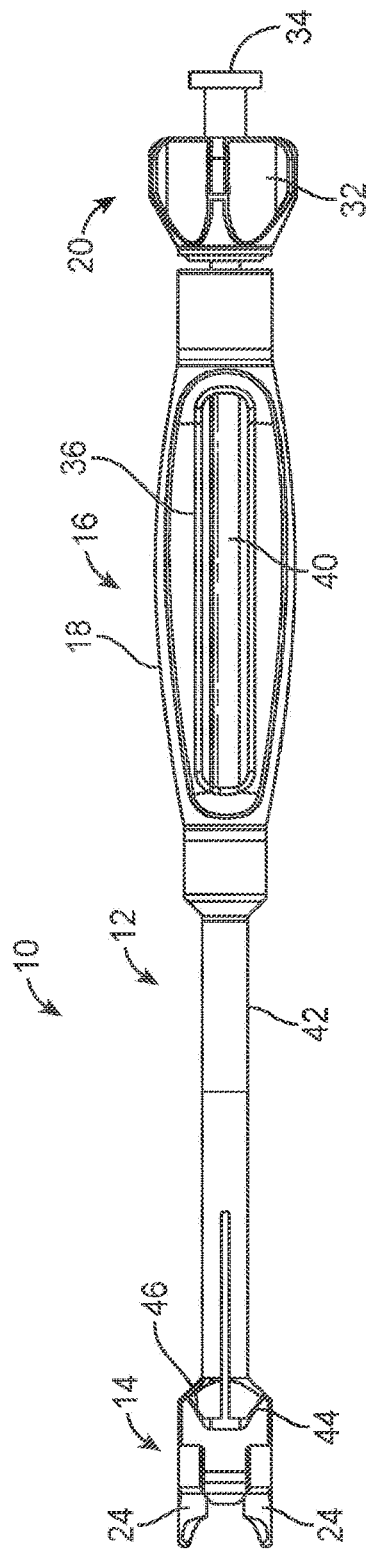
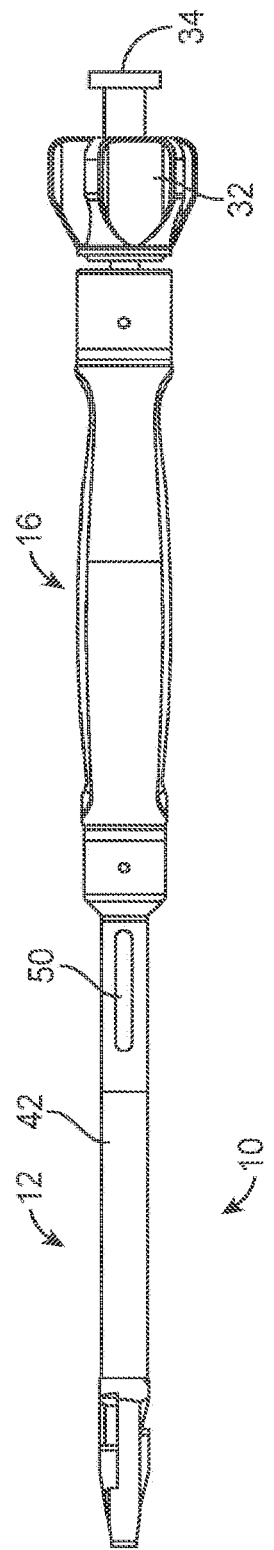
FIG. 2
FIG. 3

INTERVERTEBRAL PROSTHETIC DISC PLACEMENT AND REMOVAL SYSTEMS

CROSS-REFERENCE TO RELATED APPLICATIONS

This application is a continuation of U.S. patent application Ser. No. 16/861,079, which claims the benefit of U.S. Provisional No. 62/841,359, filed May 1, 2019, the entire contents of which are incorporated herein by reference.

BACKGROUND OF THE INVENTION

1. Field of the Invention

The present invention relates to medical devices and methods. More specifically, the invention relates to intervertebral prosthetic discs and systems and methods for implantation of an intervertebral prosthetic disc.

Back pain takes an enormous toll on the health and productivity of people around the world. According to the American Academy of Orthopedic Surgeons, approximately 80 percent of Americans will experience back pain at some time in their life. On any one day, it is estimated that 5% of the working population in America is disabled by back pain.

Common causes of back pain are injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs. With age, intervertebral disks begin to shrink. In some cases, they may collapse completely and cause the bones to rub against one another. This is also referred to as osteoarthritis.

When a damaged intervertebral disc causes a patient pain and discomfort, surgery is often required. Typically, surgical procedures for treating damaged intervertebral discs involve discectomy (partial or total removal of a disc), often followed by interbody fusion of the superior and inferior vertebrae adjacent to the disc or implantation of an intervertebral prosthetic disc. Fusion is most commonly achieved by implantation of a cage or spacer together with bone graft material to promote bone growth to fuse the adjacent vertebrae together. Oftentimes, pins, rods, screws, cages and/or the like are placed between the vertebrae to act as support structures to hold the vertebrae and bone graft material in place while the bones permanently fuse together. Spinal fusion eliminates motion between the vertebrae. Fusion is an option when motion is the source of pain.

An alternative to spinal fusion which doesn't limit patient mobility is intervertebral disc replacement (TDR), also called total disc arthroplasty. The TDR procedure involves removing the natural disk from between the vertebrae and replacing it with and artificial disc prosthesis. Several types of intervertebral disc prosthesis are currently available. For example, one type of intervertebral disc prosthesis includes upper and lower prosthesis plates which locate against and engage the adjacent vertebral bodies and a mobile core positioned between the plates. The core may be movable or fixed, metallic, ceramic or polymer and generally has at least one convex outer surface which mates with a concave recess on one of the plates in a fixed core device. In a movable core device one or both of the outer surfaces of the core may be curved. In order to implant these intervertebral discs, the natural disc is removed and the vertebrae are distracted or forced apart in order to fit the artificial disc in place. The plates may be inserted individually or together and with or without a core. It is desirable to reduce the duration of the procedure by implanting the disc in an assembled configuration. However, when holding the disc for implantation it is desirable to hold the disc securely with a placement tool without damage to the disc or surrounding anatomy and remove the tool easily from the disc which it is in the appropriate position.

Currently available intervertebral prosthetic discs are held, delivered and removed with a variety of different instruments and techniques. Challenges with these known instruments and techniques include inadvertent changes to the prosthetic disc position during disconnection of the instrument or difficulty in disconnecting the instrument from the prosthetic disc because of interference of surrounding anatomy. It would be desirable to provide a disc system with a simple placement instrument which easily and securely grasps the implant for insertion and is then easily removed from the patient.

In addition, it would be desirable to hold the disc in the implantation instrument in an articulated or angled insertion configuration to prevent the need for over distraction of the disc space.

Further, it would be desirable to provide a disc removal system with an instrument to more easily and quickly separate the components of an intervertebral prosthetic disc for removal.

Therefore, a need exists for an improved artificial intervertebral disc placement and removal systems which improve speed and reliability of the surgical procedures.

2. Description of the Background Art

A variety of intervertebral disc prosthesis designs and methods of implanting are described in described in U.S. Pat. Nos. 7,442,211; 7,531,001; 7,575,599; 7,585,326; 7,637,913; 7,753,956; 8,206,449, 8,685,035; 8,764,833; 8,808,384; 9,011,544 and 9,351,846, and U.S. patent application Ser. No. 15/842,663, each of which is incorporated herein by reference in its entirety.

BRIEF SUMMARY OF THE INVENTION

According to one aspect of the invention, an intervertebral prosthetic disc placement instrument includes an instrument shaft having a distal end and a proximal end; an instrument handle on the proximal end having an activation mechanism; and a pair of grasping jaws on the distal end of the instrument shaft. The grasping jaws are configured to move with respect to one another to grasp a multipart prosthetic disc in a non-articulating configuration. The grasping jaws are movable from a tightened to a released position by the activation mechanism A prosthetic disc ejector on the distal end of the instrument shaft moves distally with respect to the pair of grasping jaws when the grasping jaws are in the released position and the ejector is configured to contact the prosthetic disc to fully disengage the prosthetic disc from the placement instrument.

In accordance with another aspect of the invention, a method of placing an intervertebral prosthetic disc with a single placement instrument includes the steps of securing a multipart prosthetic disc to a distal end of a placement instrument by grasping at least a portion of the multipart prosthetic disc between grasping jaws on the placement instrument; inserting the prosthetic disc into a disc space of a patient with the placement instrument; releasing the prosthetic disc grasping jaws by moving the grasping jaws from a tightened to a released position by an activation mechanism on the placement instrument handle; and ejecting the prosthetic disc from the grasping jaws with a prosthetic disc ejector on the distal end of the instrument shaft which moves distally with respect to the pair of grasping jaws when the grasping jaws are in the released position and wherein the ejector is configured to contact the prosthetic disc to fully disengage the prosthetic disc from the placement instrument.

In accordance with a further aspect of the invention, an intervertebral prosthetic disc core removal instrument includes a pair of core removal arms having inner surfaces shaped to correspond substantially to a shape of an outer perimeter of a prosthetic disc core; a distraction wedge tapered from a thinnest portion at a distal end to thicker portion at some distance from the distal end such that insertion of the distraction wedge between two prosthetic disc plates of the prosthetic disc distracts the plates away from one another to allow the core to be more easily removed; and a core removal instrument handle. The instrument handle is connected to the pair of core removal arms and the distraction wedge. The handle is configured to move the arms with respect to one another to grasp the core for removal and configured to advance the distraction wedge to distract the plates away from one another to allow the core to be more easily removed.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 is a top view of the instrument of FIG. 1;

FIG. 3 is a side view of the instrument of FIG. 1;

DETAILED DESCRIPTION OF THE INVENTION

Positioning of an intervertebral prosthetic disc properly in the spine is an important part of a successfully total disc arthroplasty (TDR) procedure. The position of the implant in the intervertebral space can influence the range of motion, implant behavior and clinical result. Proper position in the anterior/posterior direction between the vertebral bodies is particularly important but can be difficult due to surrounding anatomy. Surgeon experience, surgeon training, use of imaging modalities and patient anatomy are all factors which can influence accuracy of prosthetic disc placement.

An intervertebral prosthetic disc placement system according to the present invention includes a multi-part prosthetic disc and an associated placement instrument. The placement instrument holds the prosthetic disc securely for placement into an intervertebral disc space and quickly releases the disc within the disc space at a desired position between the vertebral bodies. The quick release is facilitated by providing the instrument with an ejector which helps disengage the prosthetic disc from the instrument.

One example of an intervertebral prosthetic disc for insertion between adjacent vertebrae includes an upper plate, a lower plate and a core between the upper and lower plates, such as the prosthetic discs described in U.S. Pat. Nos. 8,808,384 and 10,206,785, which are incorporated herein by reference in their entirety. The core is retained between the upper and lower plates by a retention feature and is designed to allow the plates to slide over the upper and lower surfaces of the core in the anterior/posterior direction and in the lateral direction and to allow the plates to articulate and rotate with respect to each other and the core. The upper and lower plates are provided with a side groove, notch, slot, channel or other feature which can be grasped by the placement instrument.

Figure 1:
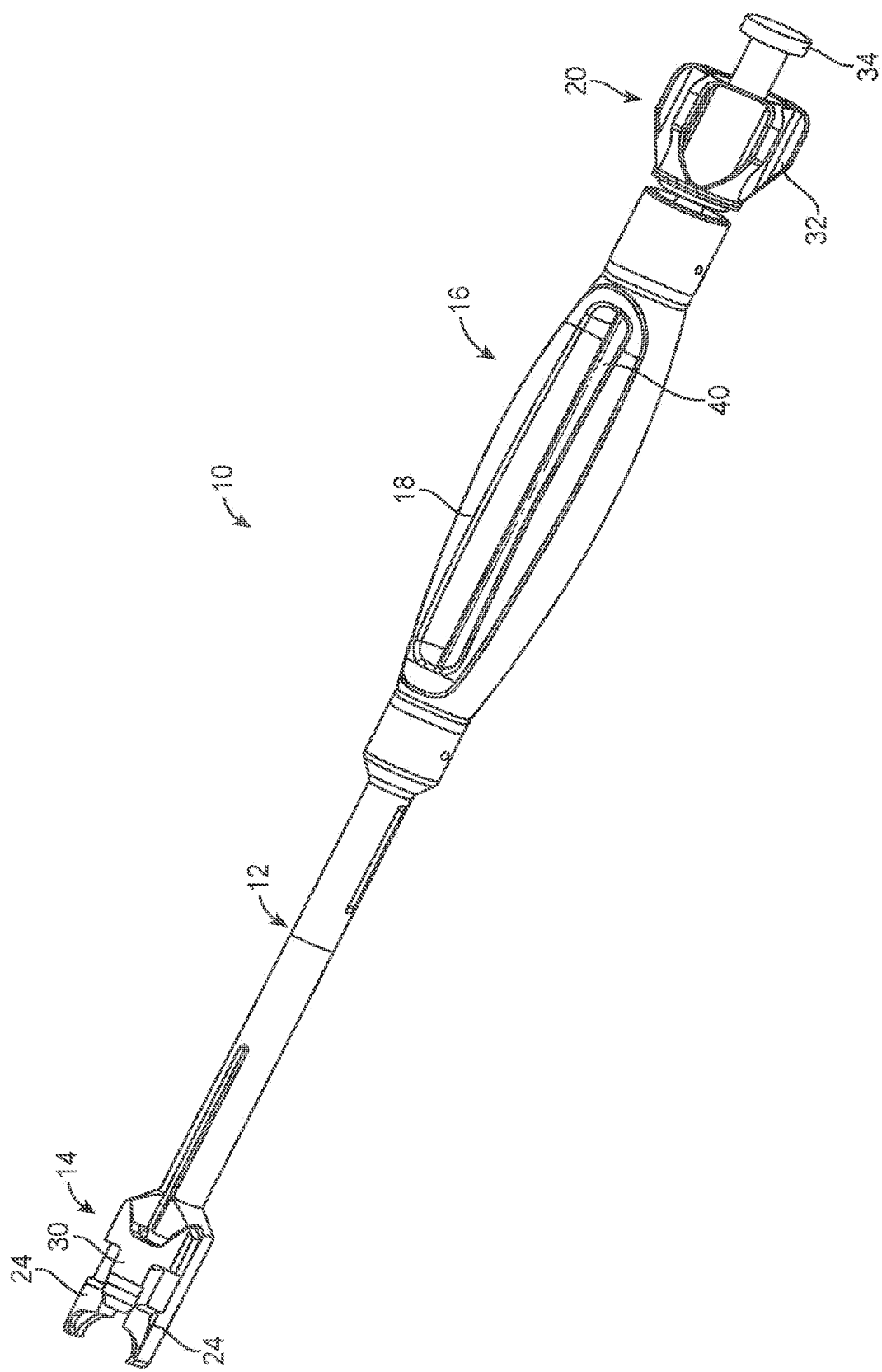
FIG. 1 is a perspective top view of an intervertebral prosthetic disc placement instrument in a loading position.

FIG. 1 illustrates a first embodiment of a prosthetic disc placement instrument 10 formed of a shaft 12, a distal end effector 14 and a proximal handle end 16. The proximal handle end 16 includes a grasping handle 18 and an activation mechanism 20. A pair of grasping jaws 24 on the distal end 14 are configured to move with respect to one another to grasp a multipart prosthetic disc. Preferably, the jaws 24 grasp the prosthetic disc from the sides of the disc in a non-articulating configuration so that the multiple parts of the prosthetic disc can be placed simultaneously. The grasping jaws 24 are movable from a loading or grasping position shown in FIG. 1 to a tightened position, a release position, an eject position and a cleaning position by the activation mechanism 20. The loading or grasping position shown in FIG. 1 has an activation mechanism nut 32 not in contact with the handle 18 allows the grasping jaws 24 to flex outward to receive the prosthetic disc. Once the prosthetic disc is in place between the jaws 24, the nut 32 is tightened against the handle 18 to hold the disc in the tightened position in the jaws. After placement of the disc in the disc space, the nut 32 is loosened to a release position which looks can be the same as the loading position and the jaws 24 are no longer tightly grasping the disc.

A prosthetic disc ejector 30 on the distal end of the instrument shaft 12 moves distally with respect to the pair of grasping jaws 24 to contact the prosthetic disc to fully disengage the prosthetic disc from the placement instrument 10. The activation mechanism 20 includes the nut 32 used to open and close the jaws 24 and a thumb activated button 34 used to advance the ejector 30.

Figure 6:
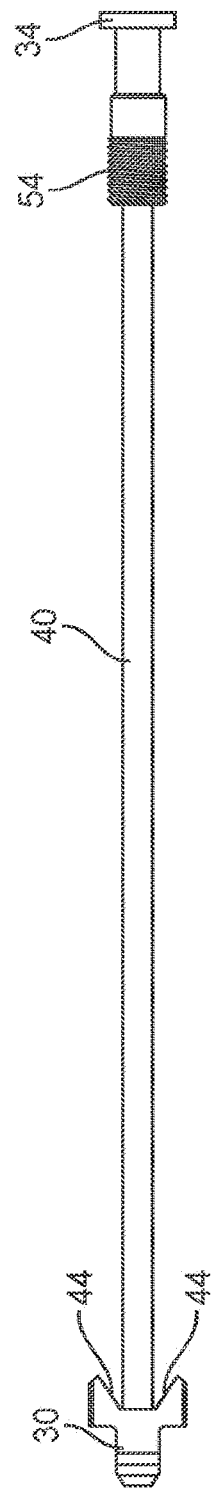
FIG. 6 is a top view of the inner ejector rod of the instrument of FIG. 1.
Figure 7:
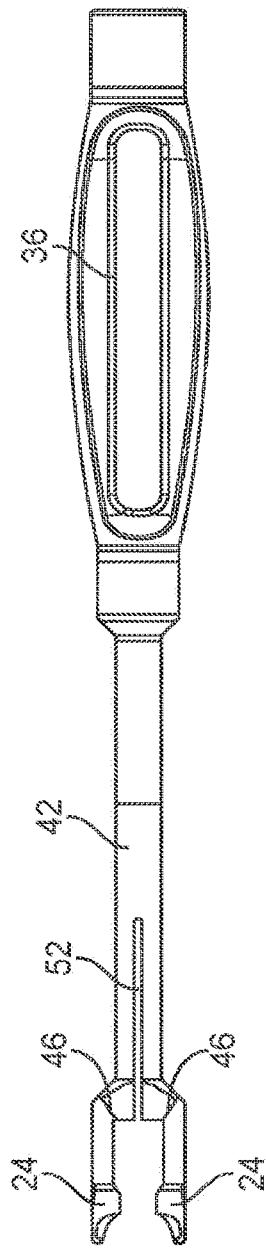
FIG. 7 is a top view of the outer handle and grasping assembly of the instrument of FIG. 1.

FIG. 2 is a top view of the placement instrument 10 with the jaws 24 shown in a loading or grasping position. In the tightened position, the distal end 14 of the instrument looks the same, but the jaws 24 securely hold the disc because the nut 32 is tightened against the proximal end of the handle 18. As can be seen through a window 36 in the handle 18, the shaft 12 is formed of an inner shaft 40 and an outer shaft 42. The inner shaft 40 has a threaded portion at the proximal end which receives the activation mechanism nut 32. The inner shaft 40 is also connected to the ejector 30 at a distal end and rotation of the nut 32 moves the inner shaft 40 within the outer shaft to loosen and tighten the jaws 24. Inner cam surfaces 44 on the ejector 30 engage the outer cam surfaces 46 on the outer shaft 42 to tighten the jaws 24 upon rotation of the nut 32. The inner and outer cam surfaces 44, 46 can be seen more clearly in FIGS. 6 and 7 which show top views of the inner ejector rod and the outer handle and grasping assembly of the instrument 10 in the disassembled configuration. Also shown clearly in FIG. 7 is the slot 52 in the outer shaft allows the movement of the jaws 24 between the loosened loading position and tightened position by flexion of a portion of the shaft. Although the jaws 24 are shown as grasping the upper and lower plates at notches in the lateral surfaces of the plates other grasping arrangements can be employed. For example, only one of the upper and lower plates can be grasped; the plates can be grasped at their upper or lower surfaces or on another grasping feature of the plates; or the grasping jaws can grasp the plates and/or the core of the prosthetic disc.

Figure 4:
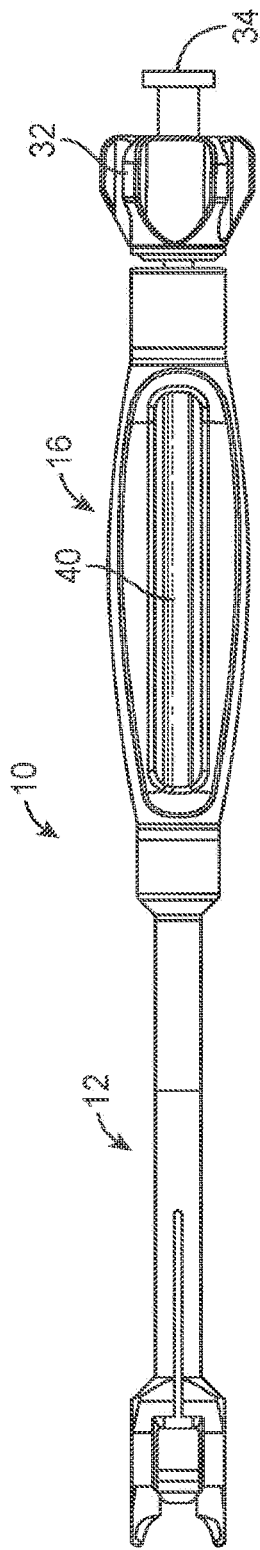
FIG. 4 is a bottom view of the instrument of FIG. 1.

FIGS. 3 and 4 are side and bottom views, respectively, of the instrument 10 in the same loading or released position of FIG. 1 with the nut 32 threaded onto threads near the proximal end of the inner shaft 40. In the fully tightened position, the nut 32 will contact a proximal end of the outer shaft 42.

Figure 5:
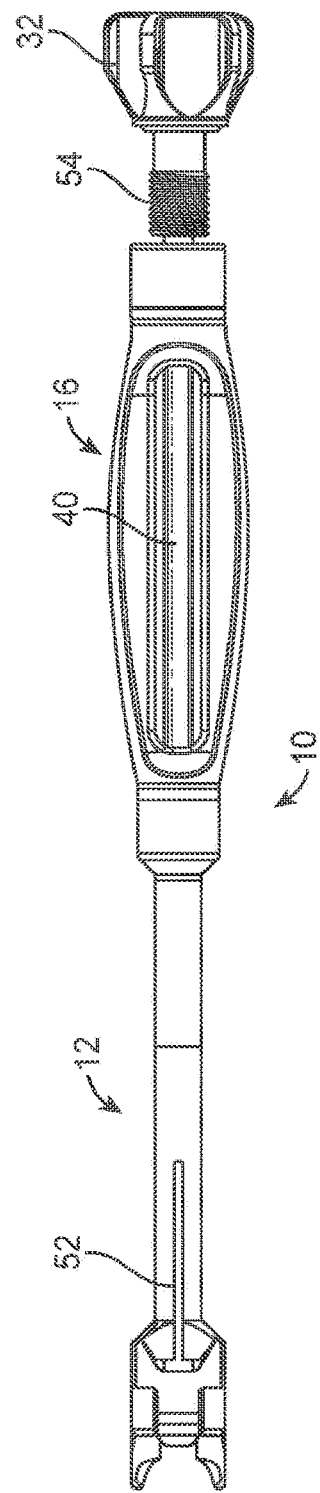
FIG. 5 is a top view of the instrument of FIG. 1 in a cleaning position.

FIG. 5 shows a top view of the instrument of 10 in a cleaning position. In the cleaning position, the nut 32 is fully unthreaded or disengaged from threads 54 of the inner shaft 40, however, the nut 32 does not fall off the instrument since it is prevented from fully separating from the instrument by the disc shaped thumb button 34 of the inner shaft. In the cleaning position, all parts of the instrument 10 are connected and unable to be completely separated and are in a loose configuration to allow cleaning fluid to pass through all parts of the instrument. The cleaning window 36 in the handle 18 and an addition cleaning window 50 (FIG. 3) and slot 52 in the outer shaft 42 assist in allowing cleaning fluid to circulate through all parts of the instrument and particularly between the inner and outer shafts and within the threads of the nut.

Figure 8:
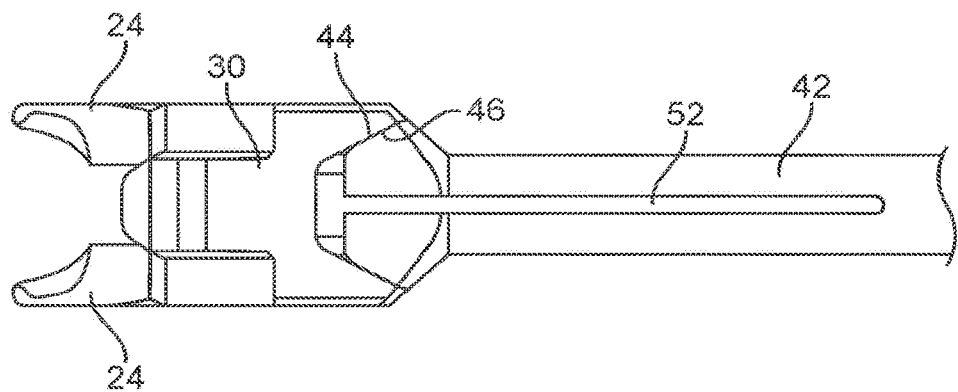
FIG. 8 is a top view of the distal end of the instrument of FIG. 1 in the loading or tightened position.
Figure 9:
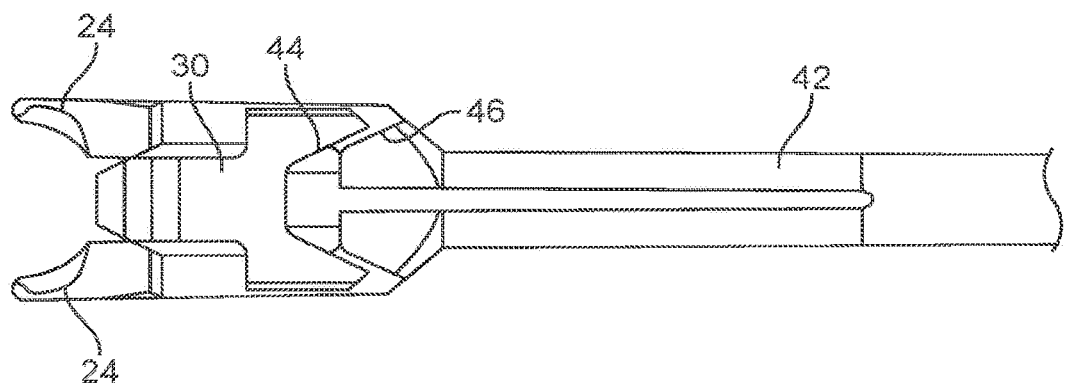
FIG. 9 is a top view of the distal end of the instrument of FIG. 1 in the release position.
Figure 10:
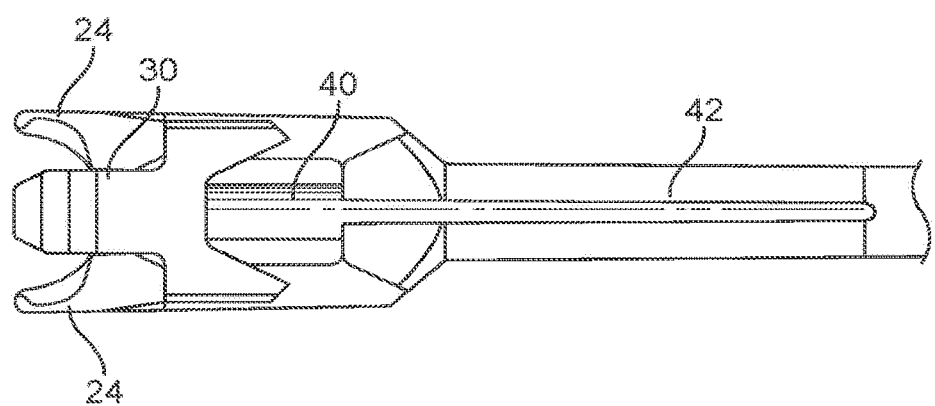
FIG. 10 is a top view of the distal end of the instrument of FIG. 1 in the ejecting position.

FIGS. 8-10 show a top view of the distal end of the instrument 10 in three different positions including the tightened position (FIG. 8); the released position (FIG. 9); and the ejecting position (FIG. 10). In the tightened position of FIG. 8, the nut pulls the inner shaft proximally sliding the inner cam surfaces 44 of the ejector against the outer cam surfaces 46 of the outer shaft 42 to move the jaws together in the grasping or tightened position. In the released or disengaged position of FIG. 9, the nut is released to allow the cam surfaces 44, 46 to disengage with one another and allow the jaws 24 to move apart out of the notches or grooves in the sides of the prosthetic disc. In the ejecting position of FIG. 10, a distal end of the ejector 30 functions to both push the jaws 24 further apart and to push the prosthetic disc off of the instrument jaws. The ejector 30 is moved forward to the ejecting position by pressing on the thumb activated button 34 at the proximal end of the instrument. The particular cam arrangement shown in FIGS. 8-10 are just one example of a cam system which can be employed to move the jaws 24 and the ejector 30 between the tightened, released and ejecting positions. In addition, a distal end of the ejector 30 can be configured to mate with and apply a force to any part of the prosthetic disc to achieve the desired separation of the instrument from the disc. For example, the ejector distal end can be configured to mate with the core, one or more of the plates or both the core and the plates.

When the ejector 30 is in the ejecting position shown in FIG. 10, the ejector can be used to adjust the position of one or more parts of the prosthetic disc or the entire prosthetic disc. For example, the distal end of the ejector 30 can be shaped to engage an upper and lower plate of the prosthetic disc to advance the upper and/or lower plate posteriorly by tapping with a mallet on the proximal end of the placement instrument 10. The use of the ejector 30 to advance the plates proximally either separately or together eliminates the need to use a separate final placement instrument to adjust the plates of the prosthetic disc to a final position between the vertebrae. In one example, the distal edge of the ejector 30 has a concave curvature to match a corresponding convex posterior edge of the upper and/or lower plates.

Figure 11:
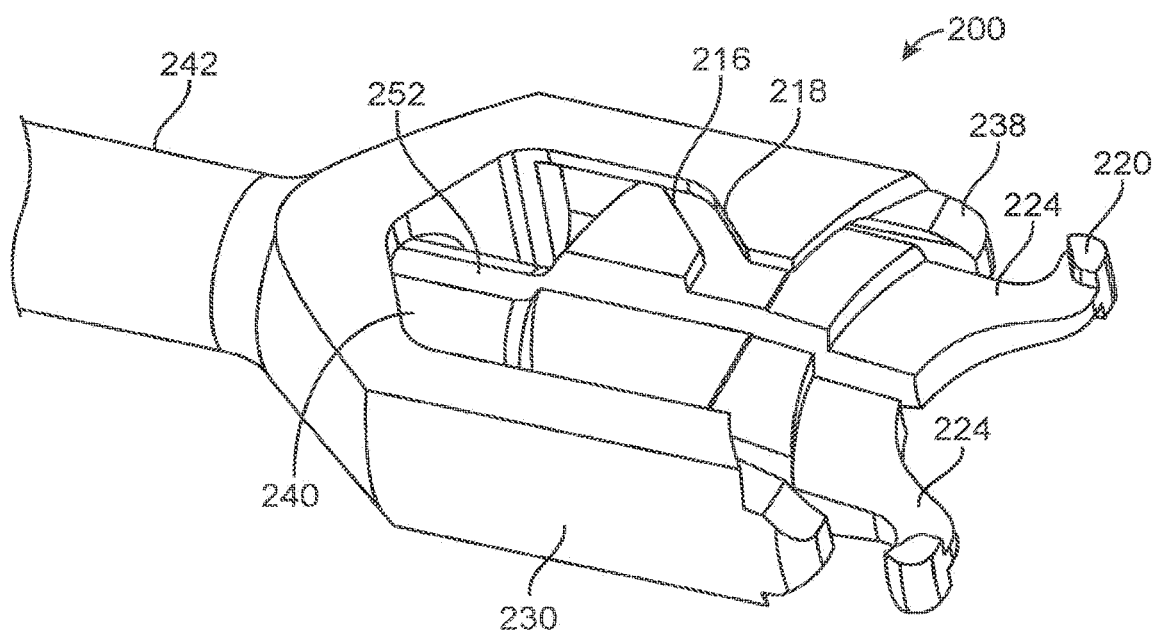
FIG. 11 is a perspective view of a distal end of an alternative embodiment of an intervertebral disc placement instrument.
Figure 12:
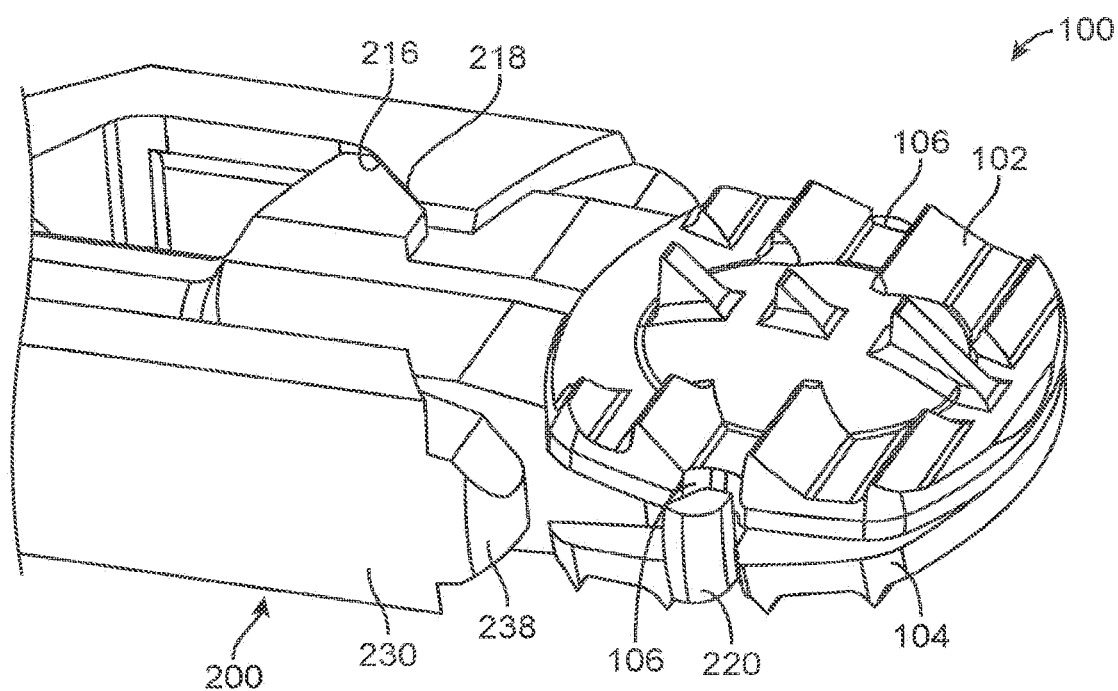
FIG. 12 is a perspective view of the instrument of FIG. 11 with a prosthetic disc locked in place on the instrument.

FIGS. 11-15 illustrate another embodiment of a placement instrument 200 with a different configuration of grasping jaws and ejector and illustrate the interaction of the placement instrument with one example of a prosthetic disc 100. As shown in FIG. 12, the prosthetic disc includes an upper plate 102, a lower plate 104 and a mobile core (not shown) between the upper and lower plates. The upper and lower plates 102, 104 articulate with respect to one another in the implanted configuration and are locked in a non-articulating insertion position when the prosthetic disc 100 is secured to the placement instrument 200. Notches 106 on the sides of the upper and lower plates 102, 103 are sized and shaped to receive the placement instrument jaws.

Similar to the embodiment of FIG. 1, the placement instrument 200 of FIGS. 11-15 includes inner and outer shafts which move with respect to one another. However, in the placement instrument 200 the inner shaft 240 is connected to the jaws 224 while the outer shaft 242 is connected to the ejector 230. FIG. 11 is a perspective view of a distal end of the placement instrument 100 without a prosthetic disc showing the jaws 224 formed on the inner shaft 240. The inner shaft 240 has a split 252 which allows the jaws 224 to flex between the tightened or locked position and the released position. In the tightened position of FIG. 12, the jaws 224 are pressed toward each other by sliding the inner shaft 240 distally within the outer shaft 242 (or sliding the outer shaft proximally over the inner shaft) to contact an inner shaft cam surface 216 with an outer shaft cam surface 218. Although a single set of cam surfaces are shown, a pair of cam surfaces can also be used. For example, cam surfaces can be provided on the other jaw on the left and right sides of the instrument or on the opposite top and bottom surfaces of the instrument. The jaws 224 of the instrument 200 are configured to be released from the upper and lower plates 102, 104 by moving laterally out of the notches 106 of the plates and/or by moving the plates apart and pulling the jaws out between the plates.

FIG. 12 is a perspective view of the instrument 200 with a prosthetic disc 100 locked in and fully tightened on the instrument with tabs 220 at the distal ends of the jaws 224 positioned within and engaging the notches 106 in the plates 102, 104. As shown in FIGS. 12-15 the plates 102, 104 are arranged for insertion in an angled configuration in which the plate edges at the posterior side of the disc (furthest away from the instrument) are closer together than the edges of the plates at the anterior side of the disc. This angled implantation position provides a wedge shape for lower force insertion. FIG. 12 shows the cam surfaces 216, 218 of the instrument engaged to hold the prosthetic disc in this wedge shape in a locked arrangement for insertion.

Figure 13:
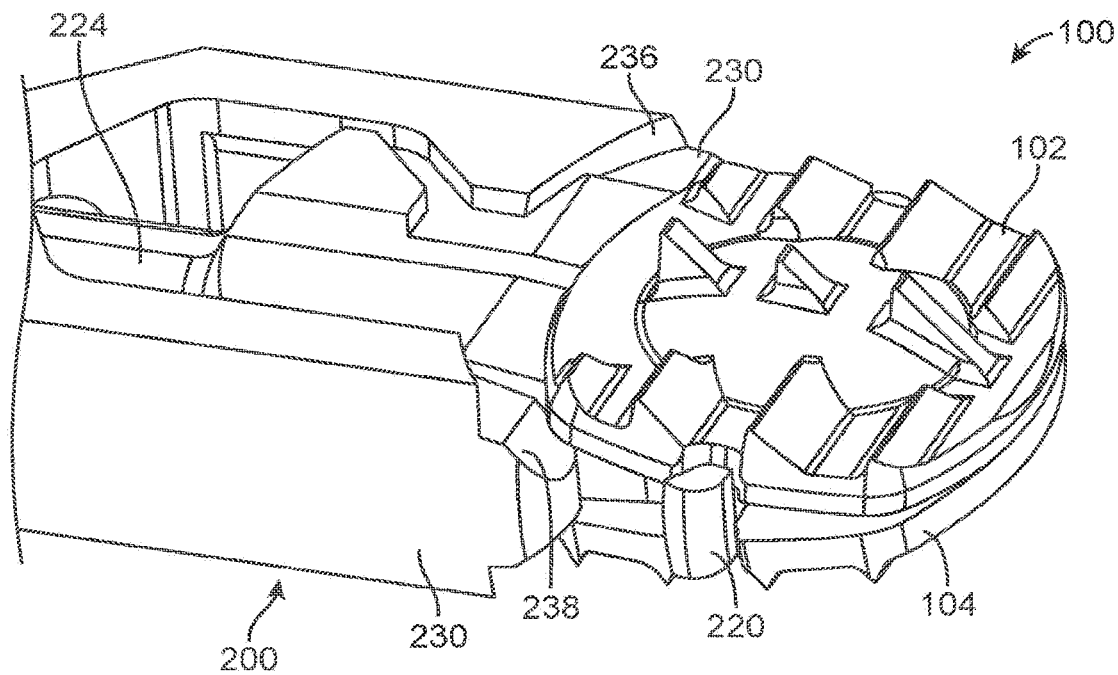
FIG. 13 is a perspective view of the instrument of FIG. 11 with the disc in the released position.
Figure 14:
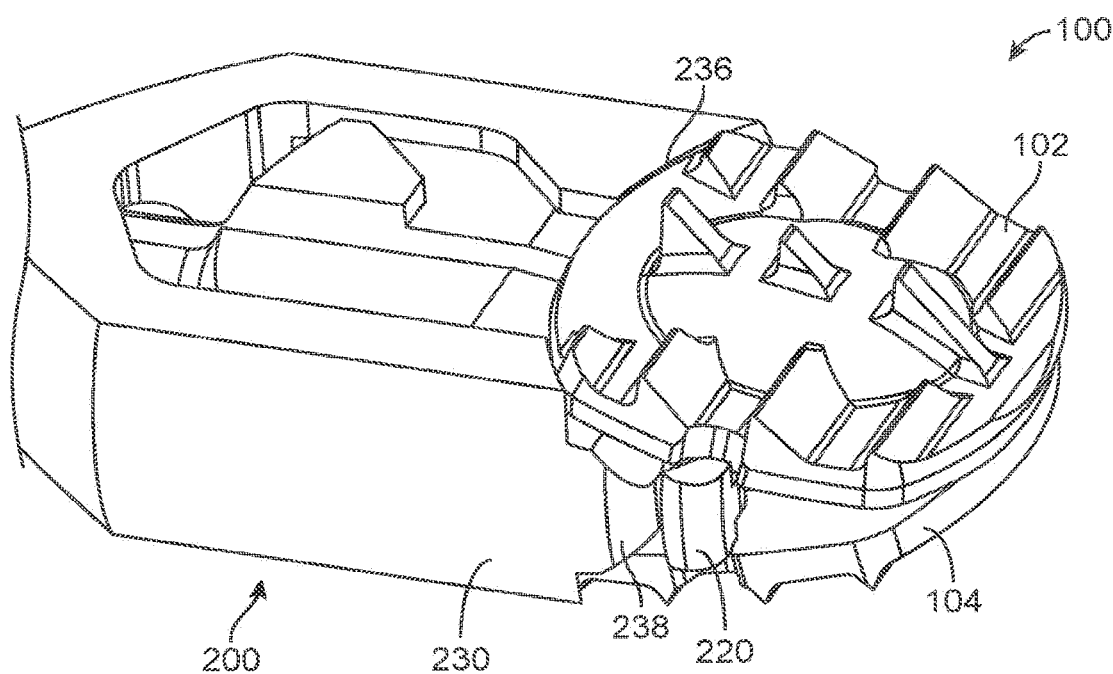
FIG. 14 is a perspective view of the instrument of FIG. 11 with the disc plates in the lifted off position.

FIG. 13 shows the instrument 200 with the inner shaft 224 starting to be pulled back within the outer shaft 242 to release the inward pressure on the tabs 220 and allow the disc 100 to be released from the instrument 200. However, although there is no inward pressure on the tabs 220 holding the disc on the instrument 200, it may not be easy to remove the instrument from the disc because the surrounding anatomy of the patient at the implant site continues to prevent to tabs 220 from fully disengaging from the plate notches 106. In the case that the instrument 200 does not easily release from the prosthetic disc 100, the ejector 230 can be used to push the disc off of the instrument. The ejector 230 includes two wedge shaped members 238 which pass between the plates 102, 104 to separate the plates and allow the plates to slip off the tabs 220. The ejector 230 also has four disc contacting surfaces 236 or abutment surfaces which engage the posterior edges of the plates 102, 104 to separate the disc from the instrument. The disc contacting surfaces 236 are preferably shaped to match the shapes of the corresponding anterior edges of the disc. FIG. 14 shows the instrument and prosthetic disc in a position in which plates are lifted off the tabs 220 by the wedge 238 of the ejector 230 and the disc contacting surfaces 236 of the ejector are in contact with the disc for ejecting.

Figure 15:
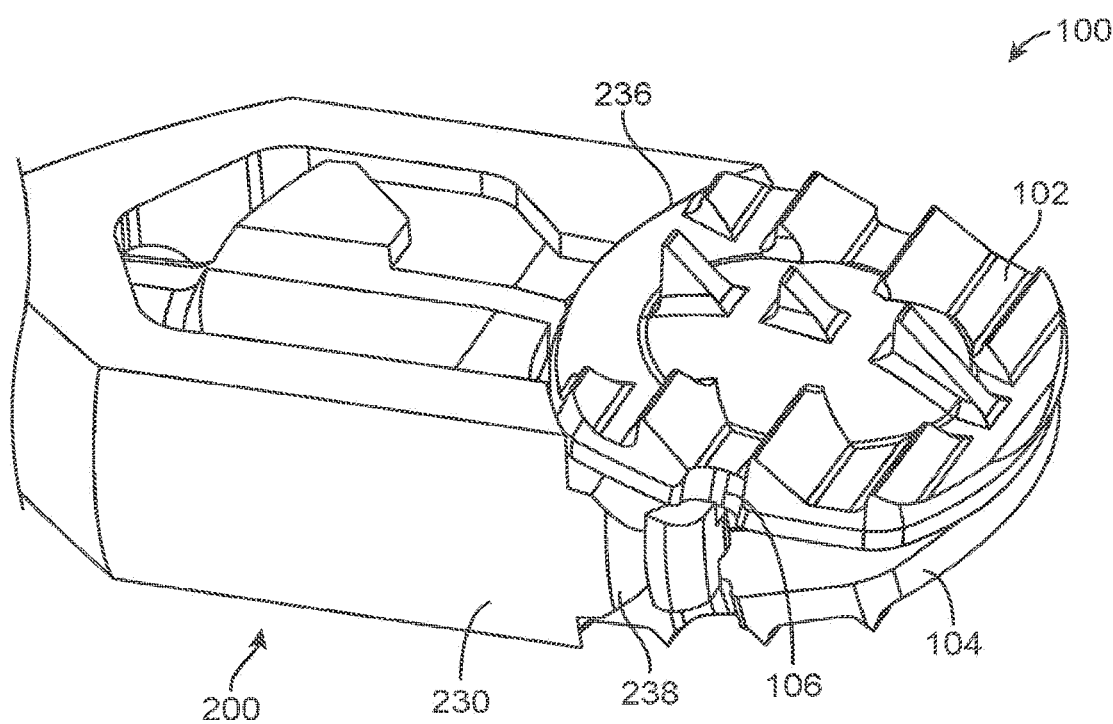
FIG. 15 is a perspective view of the instrument of FIG. 11 with the disc in the ejecting position.

FIG. 15 shows the prosthetic disc 100 in the ejecting position with the plate notches 106 popped off the tabs 220 and the plates passing over the top and bottom of the tabs of the jaws 224. This allows the jaws 224 to be drawn straight back toward the instrument and avoids any difficulty disengaging the instrument when the patient's anatomy prevents the jaws from moving laterally in the disc space. In the event that the patient's anatomy does not prevent the jaws 224 from moving laterally, the prosthetic disc 100 can be released from the jaws without the need for the ejector by drawing the jaws back away from the disc.

A method for inserting an intervertebral prosthetic disc with the placement instruments 10, 100 described herein involved securing the prosthetic disc to the instrument by tightening the instrument jaws, inserting the prosthetic disc to a desired location between the vertebrae, releasing the instrument jaws from the prosthetic disc, ejecting the disc from the instrument and removing the instrument from the patient. The intervertebral prosthetic disc is surgically implanted between adjacent spinal vertebrae in place of a damaged disc. Those skilled in the art will understand that the damaged disc is partially or totally removed according to known procedures and the adjacent vertebrae are forcibly separated from one another prior to inserting the prosthetic disc to provide the necessary space for insertion of the disc.

To connect the prosthetic disc securely in the placement instrument 10, 100, the tabs of the instrument jaws are seated in the upper and lower plate notches formed at the sides of the plates. The placement instrument is tightened around the disc by tightening the activation knob or other activation mechanism which may be at the proximal end of the handle or at another location on the handle. Once the prosthetic disc is loaded and tightened on the placement instrument the disc is inserted between the vertebral bodies with the patient lying flat on the operating table and the instrument straight up and down, perpendicular to the body. If the prosthetic disc includes fins or teeth requiring slots to be cut in the vertebral bodies, the disc is inserted with the fins or teeth aligned with the precut slots. Using lateral imaging and a mallet to tap the distal end of the placement instrument, the prosthetic disc is inserted into the space between vertebral bodies until the upper and lower plates are at or within about 1 mm of the posterior margin of the vertebral bodies. When the prosthetic disc is in the proper position as verified by X-ray or fluoroscopic imaging, the placement instrument is removed by activation of the activation mechanism. In one embodiment, the activation nut is rotated counter-clockwise until the upper and lower plates are released by the jaws. If the placement instrument is loose after releasing the jaws, the instrument can be removed. Slight side to side motion can be used to remove the instrument. However, if the instrument is not easily removed, the ejector is activated to press the implant off of the instrument. Preferably, the activation mechanism for the ejector is manually activated without the need for a mallet. The ejector in the ejecting position shown in FIG. 10 can be used as a final placement instrument to adjust the position of one or more parts of the prosthetic disc by advancing the disc posteriorly. Once the disc has been inserted to a desired position as confirmed by lateral imaging, distraction of the vertebra is released and the vertebra move together to hold the assembled disc in place.

In another version of a method for placement of a prosthetic disc, the placement instrument is tightened around the disc in the manner described above. Once the prosthetic disc is loaded and tightened on the placement instrument the disc is inserted between the vertebral bodies with the fins or teeth aligned with the precut slots. Using lateral imaging and a mallet to tap the distal end of the placement instrument, the prosthetic disc is inserted into the space between vertebral bodies until the disc is about half way into the space as viewed on lateral fluoroscopy, just past 50% of the anterior/posterior depth or until the jaws come into contact with the vertebral body. When the prosthetic disc is in the proper position as verified by X-ray or fluoroscopic imaging, the placement instrument is removed. The ejector in the ejecting position shown in FIG. 10 is used as a final placement instrument to advance the prosthetic disc posteriorly. Advancement may be performed by contacting one or both articulating plates of the prosthetic disc to advance the prosthetic disc either all together or by sequential advancement of upper and lower plates to a final position.

The activation mechanisms used for both the jaws and the ejectors in each of the embodiments of the placement instrument can include any of the known handle mounted activator mechanisms for instruments including one or more rotatable knobs, movable levers or other known mechanisms.

The prosthetic disc can be inserted laterally, from an anterior side, or from a posterior or posterior/lateral side of the patient's spine. In the embodiment shown, the disc is designed for insertion anteriorly into an intervertebral space. Although the disc has been described herein as inserted anteriorly and is shown in a size appropriate for the cervical spine, the system can be modified to accommodate other locations in the spine, such as the lumbar spine, and other implantation approaches.

Figure 16:
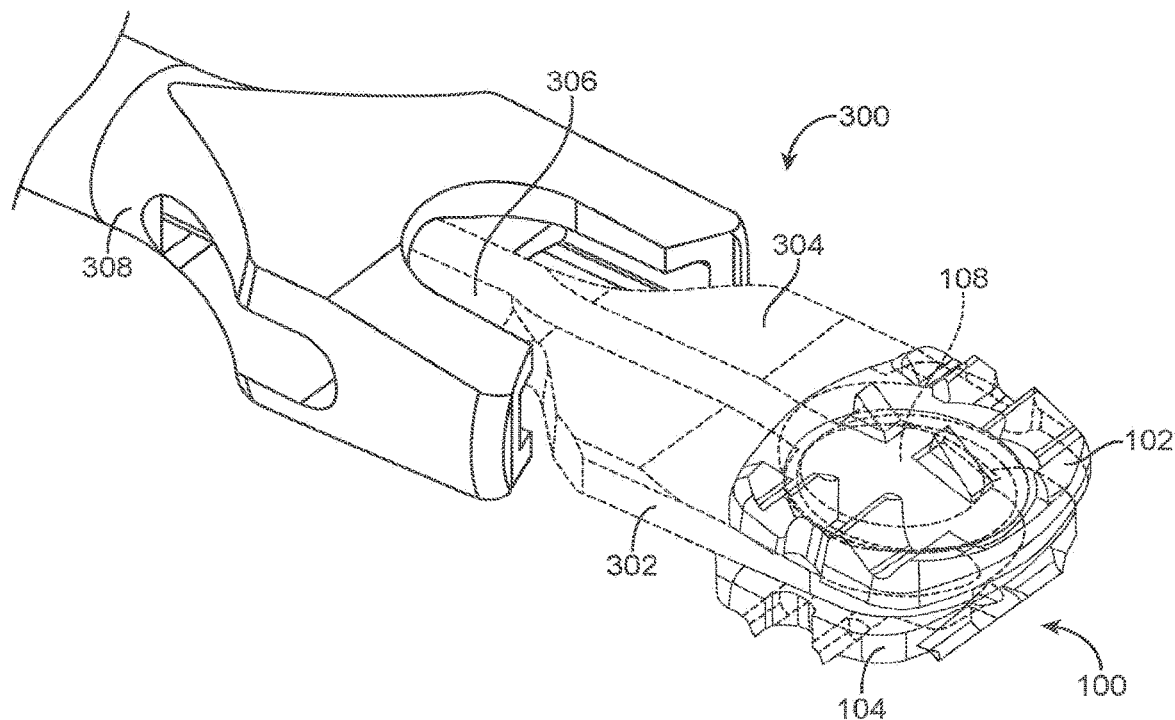
FIG. 16 is a perspective view of a core removal instrument grasping a core of a disc.

Occasionally an implanted intervertebral prosthetic disc needs to be surgically removed from a patient. Currently intervertebral prosthetic discs are removed with a variety of different instruments and techniques. Often disc removal surgery involves removing each plate from the vertebrae separately. One challenge with this known technique is that the plates are difficult to remove without significantly distracting the vertebrae. Excessive distraction of the vertebra is undesirable because of the stretching and damage to the adjacent ligaments and structures. The plates are much easier to remove from the vertebrae and distraction is minimized if the core is first removed from between the plates. A core removal instrument 300 is shown in FIG. 16. The core removal instrument 300 can grasp and remove a core 108 from between the upper and lower plates 102, 104 of the disc 100.

Figure 17:
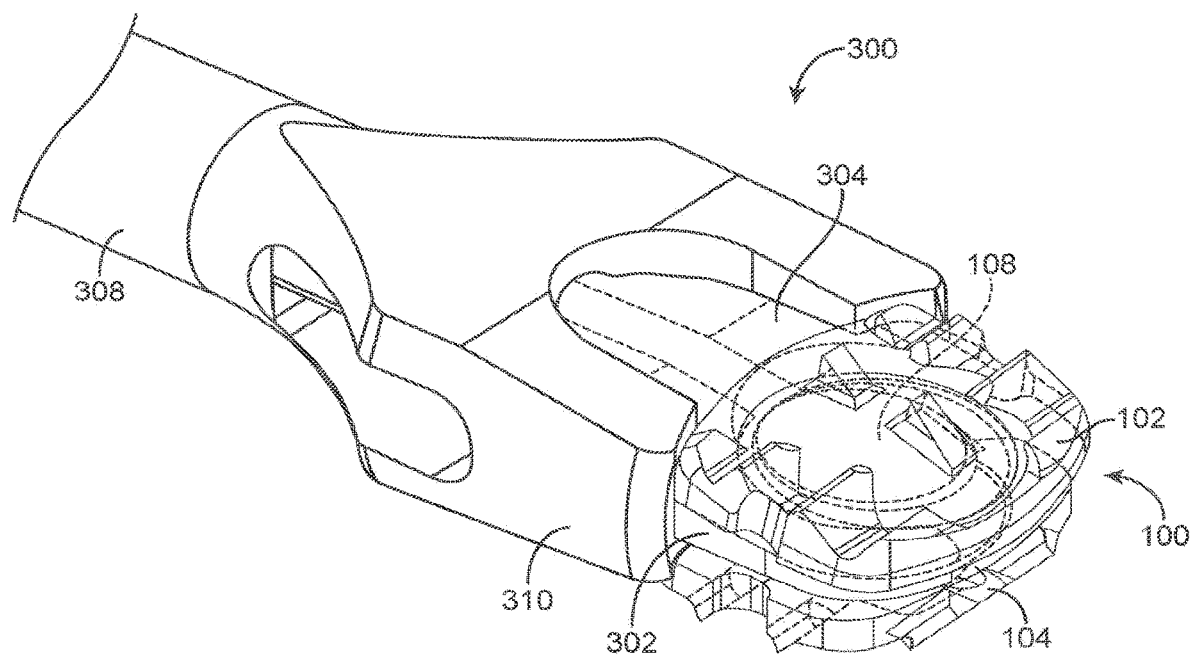
FIG. 17 is a perspective view of the instrument of FIG. 16 with the instrument removing the core.

FIGS. 16 and 17 are perspective views of the core removal instrument 300 with the instrument in the grasping position and the removing position, respectively. The core removal instrument 300 includes a pair of core removal arms 302, 304 having inner surfaces shaped to correspond substantially to a shape of the outer perimeter of the core. The shapes of the two core removal arms 302, 304 can be mirror images of one another or can be different shapes, as shown. The arms 302, 304 in one embodiment are tapered from a thinnest portion at their distal ends to thicker portion at some distance from the distal end to allow the arms to act like wedges to separate the plates 102, 104 a distance which will allow the core to be removed from between the plates. The thicker portion of the arms 302, 304 is at least two times as thick as the thinnest portion and the thicker portion is located a distance from the thinnest portion that corresponds substantially to a diameter or largest dimension of the core. Insertion of the arms 302, 304 between the disc plates distracts the plates away from one another to allow the core to be more easily removed.

The arms 302, 304 of the core removal tool 300 are connected to an inner shaft 306 of the core removal tool 300 which slides within an outer shaft 308. Any known activation mechanism can be used to move the inner and outer shafts with respect to one another including knobs, levers, cams, ratchets or the like. Distal motion of the inner shaft 306 within the outer shaft 308 to the position shown in FIG. 17 causes the arms 302, 304 to securely hold the core for removal from the plates and causes the plates 102, 104 to abut an outer housing 310 at the end of the outer shaft. The outer housing 310 holds the plates in place as the arms 302, 304 withdraw the core from between the plates.

In an alternative embodiment, the core removal tool arms and distraction wedge can be separate members which move with respect to one another and can be activated sequentially or simultaneously to grasp the core and separate the plates. In one embodiment, the core removal tool sequentially allows the surgeon to grasp the core, distract the plates and then pull out the core from between the plates. The pulling of the core out from between the plates can be performed by an activation mechanism of the handle or manually by the surgeon with the core grasped by the core removal tool arms.

Modification of the above-described assemblies and methods for carrying out the invention, combinations between different variations as practicable, and variations of aspects of the invention that are obvious to those of skill in the art are intended to be within the scope of the invention disclosure.

What is claimed is:

1. A system for removing a core from an intervertebral prosthetic disc, the system comprising:
  a core removal instrument including:
  a pair of core removal arms having inner surfaces shaped to correspond substantially to a shape of an outer perimeter of a prosthetic disc core, wherein the arms are each tapered from a thinnest portion at their distal ends to a thicker portion at some distance from the distal end such that insertion of the arms between two prosthetic disc plates distracts the plates away from one another to allow the core to be removed; and
  an inner shaft connected to the pair of core removal arms;
  an outer shaft movable with respect to the inner shaft and including an activation mechanism for causing the arms to grasp the core for removal, the outer shaft having an axial channel shaped to slidably engage an outer surface of the pair of core removal arms at the thicker portion thereof, such that the pair of core removal arms are selectively seated within the outer shaft; and
  a prosthetic disc comprising:
    an upper plate and a lower plate, wherein the upper and lower plates are configured to articulate with respect to one another and wherein the pair of core removal arms are configured to grasp the upper and lower plates in the non-articulating configuration.

2. The system of claim 1, wherein the thicker portion of the pair of core removal arms is at least two times as thick as the thinnest portion and the thicker portion is located a distance from the thinnest portion that corresponds substantially to a diameter or largest dimension of the core.

3. The system of claim 1, wherein the thicker portion is located a distance from the thinnest portion that corresponds substantially to a diameter or largest dimension of the core.

4. The system of claim 1, wherein the activation mechanism includes one of a knob, a lever, a cam, or a ratchet.

5. The system of claim 1, wherein the prosthetic disc further includes:
  the upper plate having an upper vertebra contacting surface and a lower surface having a bearing surface thereon;
  the lower plate having a lower vertebra contacting surface and an upper surface having a bearing surface thereon, wherein the upper and lower plates are configured to articulate with respect to one another;
  first and second notches in lateral surfaces of the upper plate and third and fourth notches in lateral surfaces of the lower plate, wherein the first and third notches are aligned with one another, the second and fourth notches are aligned with one another and the core removal arms are configured to grasp the upper and lower plates in the non-articulating configuration by engaging the first, second, third and fourth notches.

6. A system for removing a core from an intervertebral prosthetic disc, the system comprising:
  a core removal instrument including:
  a pair of core removal arms having inner surfaces shaped to correspond substantially to a shape of an outer perimeter of a prosthetic disc core;
  a pair of distraction wedges, each wedge being tapered from a thinnest portion at a distal end of a respective one of the pair of core removal arms to a thicker portion at some distance from the distal end, the thicker portion extending outward along an axis perpendicular to an axial orientation of the pair of removal arms, such that insertion of the distraction wedge between two prosthetic disc plates of the prosthetic disc distracts the plates away from one another to allow the core to be removed; and
  a core removal instrument handle connected to the pair of core removal arms and the distraction wedge, the handle configured to move the arms with respect to one another to grasp the core for removal and configured to advance the distraction wedge from a distal end of the core removal handle and distract the plates away from one another to allow the core to be removed; and a prosthetic disc comprising:

an upper plate and a lower plate, wherein the upper and lower plates are configured to articulate with respect to one another and wherein the pair of core removal arms are configured to grasp the upper and lower plates in the non-articulating configuration.

7. The system of claim 6, wherein the distraction wedge is formed integral with the core removal arms.

8. The system of claim 6, wherein the core removal instrument is configured to hold the plates in place as the pair of core removal arms withdraw the core from between the plates by activation of the core removal instrument.

9. The system of claim 6, further comprising an activation mechanism coupled to the pair of core removal arms for pulling of the core out from between the plates.

10. The system of claim 6, wherein the prosthetic disc further includes:

the upper plate having an upper vertebra contacting surface and a lower surface having a bearing surface thereon;

the lower plate having a lower vertebra contacting surface and an upper surface having a bearing surface thereon, wherein the upper and lower plates are configured to articulate with respect to one another;

first and second notches in lateral surfaces of the upper plate and third and fourth notches in lateral surfaces of the lower plate, wherein the first and third notches are aligned with one another, the second and fourth notches are aligned with one another and the pair of core removal arms are configured to grasp the upper and lower plates in the non-articulating configuration by engaging the first, second, third and fourth notches.

* * * * *